United States Patent
Seeman et al.

(10) Patent No.: US 7,622,567 B2
(45) Date of Patent: *Nov. 24, 2009

(54) MULTIDIMENSIONAL ORGANIZATION OF HETEROMOLECULES BY ROBUST DNA MOTIFS

(75) Inventors: Nadrian C. Seeman, New York, NY (US); Jiwen Zheng, Edison, NJ (US); Pamela E. Constantinou, Houston, TX (US)

(73) Assignee: New York University, New York, NY (US)

( * ) Notice: Subject to any disclaimer, the term of this patent is extended or adjusted under 35 U.S.C. 154(b) by 173 days.

This patent is subject to a terminal disclaimer.

(21) Appl. No.: 11/626,184

(22) Filed: Jan. 23, 2007

(65) Prior Publication Data

US 2008/0003597 A1 Jan. 3, 2008

Related U.S. Application Data

(60) Provisional application No. 60/760,929, filed on Jan. 23, 2006.

(51) Int. Cl.
*C07H 21/04* (2006.01)

(52) U.S. Cl. .................... 536/23.1; 536/24.2; 536/25.6; 977/707; 977/773; 977/792; 977/795

(58) Field of Classification Search ...................... None
See application file for complete search history.

(56) References Cited

U.S. PATENT DOCUMENTS

| | | | | |
|---|---|---|---|---|
| 6,255,469 | B1 * | 7/2001 | Seeman et al. | 536/23.1 |
| 6,430,511 | B1 * | 8/2002 | Tour et al. | 702/19 |
| 2006/0078910 | A1 * | 4/2006 | Seeman et al. | 435/6 |

OTHER PUBLICATIONS

LaBean et al "Construction, analysis, ligation and self-assembly of DNA triple crossover complexes" J. Am. Chem. Soc, 2000 122: 1848-1860.*
Ding et al "Pseudohexagonal 2D DNA crystals from double crossover cohesion" J. Am. Chem. Soc., 2004, 126: 10230-10231.*

* cited by examiner

*Primary Examiner*—BJ Forman
(74) *Attorney, Agent, or Firm*—Browdy & Neimark, PLLC

(57) ABSTRACT

Two dimensional polynucleic acid arrays are assembled from robust nucleic acid motifs as polygonal units. The polygonal units in an array have edges composed of nucleic acid multi-crossover domains and are joined together by double cohesion of adjacent polygonal units. A subset of polygonal units in the array have a nanoparticle or pendant molecule attached to an end of one edge of each polygonal unit within this subset.

20 Claims, 8 Drawing Sheets

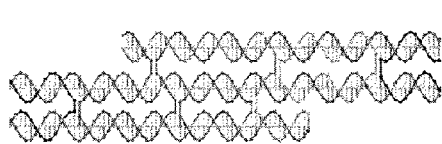
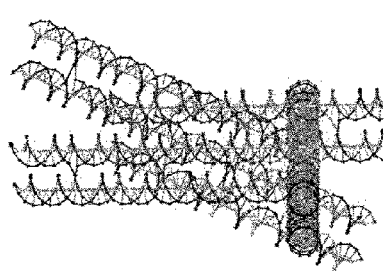
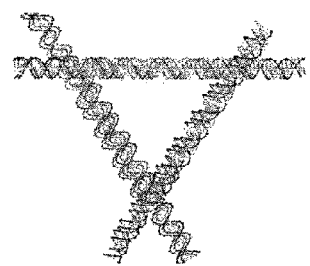
FIG. 7A  FIG. 7B  FIG. 7C
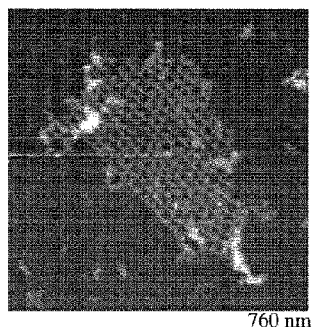
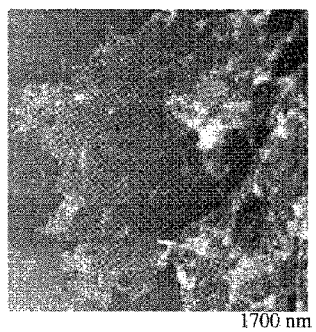
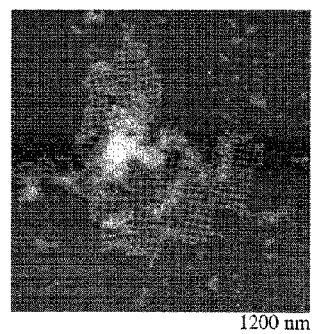
FIG. 8A  FIG. 8B  FIG. 8C

The Six-Helix Bundle
FIG. 9A  FIG. 9B
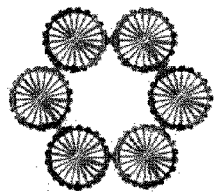
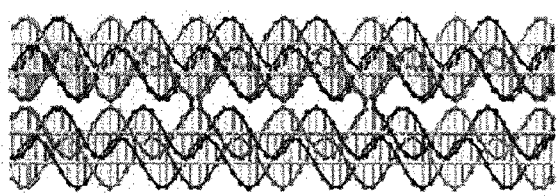
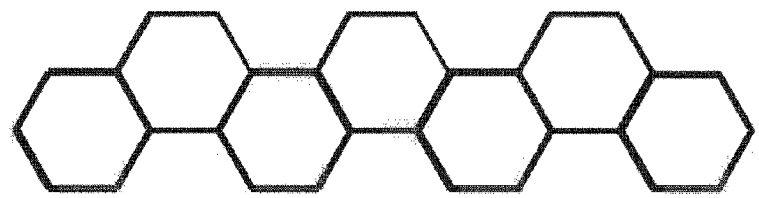
FIG. 9C
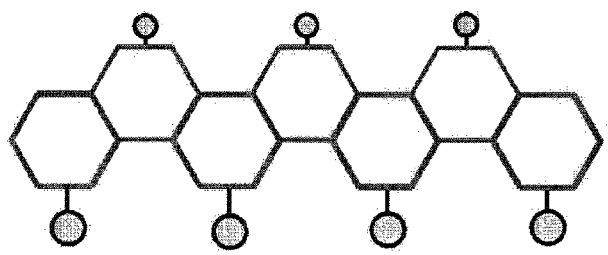
FIG. 10A
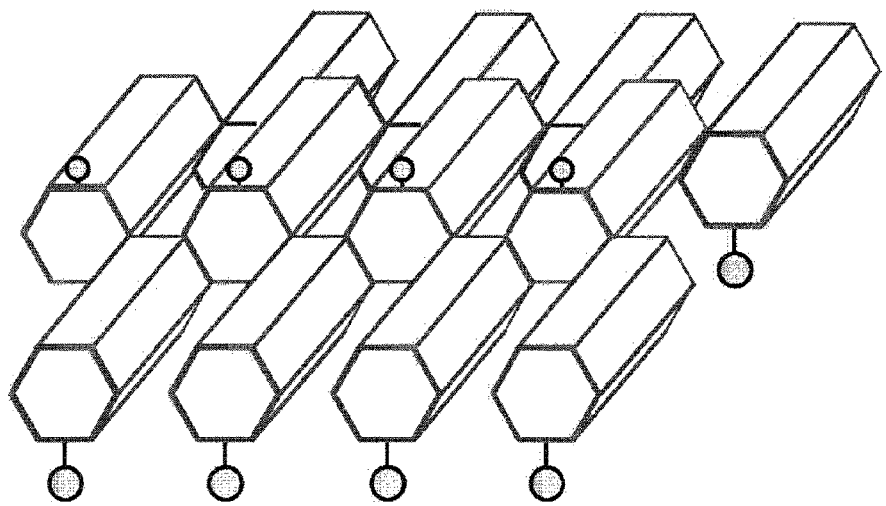
FIG. 10B 324.3*324.3 nm 324.3*324.3 nm 441.3*441.3 nm 565.5*565.5 nm 712.6*712.6 nm 463.6*463.6 nm

SEQUENCE LISTING

```
<160> NUMBER OF SEQ ID NOS: 44

<210> SEQ ID NO 1
<211> LENGTH: 72
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 1 of DXT-A

<400> SEQUENCE: 1
cgacggatga cctgatcgct acgcatcgaa cagtagtaca gaatggactt gaggcgtcaa      60
ctggacgagt tc                                                         72

<210> SEQ ID NO 2
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 2 of DXT-A

<400> SEQUENCE: 2
gaactcgtgg tcatccgtcg                                                 20

<210> SEQ ID NO 3
<211> LENGTH: 53
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 3 of DXT-A

<400> SEQUENCE: 3
gctgttggac actgcacgct ctacatcatc taagtagaca aggtggctat acc            53

<210> SEQ ID NO 4
<211> LENGTH: 76
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 4 of DXT-A

<400> SEQUENCE: 4
```

```
gatgcaatct acctgccgaa gatggcttac ctgtctcgca ccaacagcag agcataggct    60
tgaacggact catgcg                                                   76

<210> SEQ ID NO 5
<211> LENGTH: 81
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 5 of DXT-A

<400> SEQUENCE: 5
gctcctgcga gacaccattc tgccgtattc ggacatagtc accgttgtac cgacgtagga    60
cgtactcacc agctaaacgc t                                             81

<210> SEQ ID NO 6
<211> LENGTH: 22
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 6 of DXT-A

<400> SEQUENCE: 6
tagccgcatg agtggtagat tg                                            22

<210> SEQ ID NO 7
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 7 of DXT-A

<400> SEQUENCE: 7
atacaccgaa tacggtcacg                                               20

<210> SEQ ID NO 8
<211> LENGTH: 76
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 8 of DXT-A

<400> SEQUENCE: 8
acgccaatcc aggactgaat cgtcgctcgc ctgactatgt ggcgattgat attgtagtcg    60
tctatcctgt gcgttg                                                   76

<210> SEQ ID NO 9
<211> LENGTH: 72
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 9 of DXT-A
```

-continued

<400> SEQUENCE: 9
gtagcttgtg cctgtcacat cgttatgatc cgagatgtta caacggacta gactgcgata   60
gcggacgttg ag   72

<210> SEQ ID NO 10
<211> LENGTH: 22
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 10 of DXT-A

<400> SEQUENCE: 10
caacgcacac ctggattggc gt   22

<210> SEQ ID NO 11
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 11 of DXT-A

<400> SEQUENCE: 11
agtgctcaac gtggcacaag   20

<210> SEQ ID NO 12
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 12 of DXT-A

<400> SEQUENCE: 12
atgcacctac gtcggctgac   20

<210> SEQ ID NO 13
<211> LENGTH: 76
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 13 of DXT-A

<400> SEQUENCE: 13
ctgcggttca tggacggtaa ctgccagatc ctgagtacgt ggcatatcta gcatcagcga   60
gtgttcctgc ttgctc   76

<210> SEQ ID NO 14
<211> LENGTH: 72
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 14 of DXT-A -continued

```
<400> SEQUENCE: 14
gctcgactgt ggaccttgtc tacttagatg atgtagagtt agctggacgc agataggtat      60
agcctggtta ag                                                          72

<210> SEQ ID NO 15
<211> LENGTH: 22
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 15 of DXT-A

<400> SEQUENCE: 15
tcgtgagcaa gcaccatgaa cc                                               22

<210> SEQ ID NO 16
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 16 of DXT-A

<400> SEQUENCE: 16
agtgtggagc agcgtcgtgc                                                  20

<210> SEQ ID NO 17
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 17 of DXT-A

<400> SEQUENCE: 17
gtcacttaac caccacagtc                                                  20

<210> SEQ ID NO 18
<211> LENGTH: 46
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 18 of DXT-A

<400> SEQUENCE: 18
tatctgcgtg gatctggcag ttaccgtgga acactcgctg atgcta                     46

<210> SEQ ID NO 19
<211> LENGTH: 53
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 19 of DXT-A

<400> SEQUENCE: 19
```
gatatgcctg catgtcagac atctcggatc ataacgatgt gacaccgcta tcg        53

<210> SEQ ID NO 20
<211> LENGTH: 46
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 20 of DXT-A

<400> SEQUENCE: 20
cagtctagtg gcgagcgacg attcagtgga tagacgacta caatat              46

<210> SEQ ID NO 21
<211> LENGTH: 53
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 21 of DXT-A

<400> SEQUENCE: 21
caatcgcctg tatcgtgata ctactgttcg atgcgtagcg atcaccagtt gac        53

<210> SEQ ID NO 22
<211> LENGTH: 46
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 22 of DXT-A

<400> SEQUENCE: 22
gcctcaagtg gtaagccatc ttcggcaccg ttcaagccta tgctct              46

<210> SEQ ID NO 23
<211> LENGTH: 72
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 1 of DXT-B

<400> SEQUENCE: 23
ccatccgtaa cctgatcgct acgcatcgaa cagtagtaca gaatggactt gaggcgtcaa   60
ctggacgtac tc                                                   72

<210> SEQ ID NO 24
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 2 of DXT-B

<400> SEQUENCE: 24
gagtacgtgg ttacggatgg                                           20

```
<210> SEQ ID NO 25
<211> LENGTH: 53
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 3 of DXT-B

<400> SEQUENCE: 25
gctgttggac actgcacgct ctacatcatc taagtagaca aggtggctat acc        53

<210> SEQ ID NO 26
<211> LENGTH: 76
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 4 of DXT-B

<400> SEQUENCE: 26
tgacgttgcg acctgccgaa gatggcttac ctgtctcgca ccaacagcag agcataggct   60
tgaacggact ccagcg                                                  76

<210> SEQ ID NO 27
<211> LENGTH: 81
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 5 of DXT-B

<400> SEQUENCE: 27
gctcctgcga gacaccattc tgccgtattc ggacatagtc accgttgtac cgacgtagga   60
cgtactcacc agctaaacgc t                                            81

<210> SEQ ID NO 28
<211> LENGTH: 22
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 6 of DXT-B

<400> SEQUENCE: 28
gagccgctgg agtggtcgca ac                                           22

<210> SEQ ID NO 29
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 7 of DXT-B

<400> SEQUENCE: 29
atacaccgaa tacggtcacg                                              20
```

```
<210> SEQ ID NO 30
<211> LENGTH: 76
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 8 of DXT-B

<400> SEQUENCE: 30
agcaaccgcc aggactgaat cgtcgctcgc ctgactatgt ggcgattgat attgtagtcg    60
tctatcctgt gaagct                                                    76

<210> SEQ ID NO 31
<211> LENGTH: 72
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 9 of DXT-B

<400> SEQUENCE: 31
acgagcacag cctgtcacat cgttatgatc cgagatgtta caacggacta gactgcgata    60
gcggacgaag tg                                                        72

<210> SEQ ID NO 32
<211> LENGTH: 22
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 10 of DXT-B

<400> SEQUENCE: 32
agcttcacac ctggcggttg ct                                             22

<210> SEQ ID NO 33
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 11 of DXT-B

<400> SEQUENCE: 33
gcagcacttc gtggctgtgc                                                20

<210> SEQ ID NO 34
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 12 of DXT-B

<400> SEQUENCE: 34
atgcacctac gtcggctgac                                                20
```

<210> SEQ ID NO 35
<211> LENGTH: 76
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 13 of DXT-B

<400> SEQUENCE: 35
cactgtcgta tggacggtaa ctgccagatc ctgagtacgt ggcatatcta gcatcagcga     60
gtgttcctgc tacctc                                                    76

<210> SEQ ID NO 36
<211> LENGTH: 72
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 14 of DXT-B

<400> SEQUENCE: 36
gctactctgt ggaccttgtc tacttagatg atgtagagtt agctggacgc agataggtat     60
agcctggtat tg                                                        72

<210> SEQ ID NO 37
<211> LENGTH: 22
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 15 of DXT-B

<400> SEQUENCE: 37
ctacgaggta gcaccatacg ac                                             22

<210> SEQ ID NO 38
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 16 of DXT-B

<400> SEQUENCE: 38
agtgtggagc agcgtcgtgc                                                20

<210> SEQ ID NO 39
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 17 of DXT-B

<400> SEQUENCE: 39
catccaatac caccacagag                                                20

```
<210> SEQ ID NO 40
<211> LENGTH: 46
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 18 of DXT-B

<400> SEQUENCE: 40
tatctgcgtg gatctggcag ttaccgtgga acactcgctg atgcta           46

<210> SEQ ID NO 41
<211> LENGTH: 53
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 19 of DXT-B

<400> SEQUENCE: 41
gatatgcctg catgtcagac atctcggatc ataacgatgt gacaccgcta tcg    53

<210> SEQ ID NO 42
<211> LENGTH: 46
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 20 of DXT-B

<400> SEQUENCE: 42
cagtctagtg gcgagcgacg attcagtgga tagacgacta caatat           46

<210> SEQ ID NO 43
<211> LENGTH: 53
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 21 of DXT-B

<400> SEQUENCE: 43
caatcgcctg tatcgtgata ctactgttcg atgcgtagcg atcaccagtt gac    53

<210> SEQ ID NO 44
<211> LENGTH: 46
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 22 of DXT-B

<400> SEQUENCE: 44
gcctcaagtg gtaagccatc ttcggcaccg ttcaagccta tgctct           46
```

MULTIDIMENSIONAL ORGANIZATION OF HETEROMOLECULES BY ROBUST DNA MOTIFS

CROSS-REFERENCE TO RELATED APPLICATIONS

The present application claims the benefit of priority under 35 U.S.C. §119(e) from U.S. provisional application No. 60/760,929, filed Jan. 23, 2006, the entire contents of which are hereby incorporated by reference.

GOVERNMENT LICENSE RIGHTS

The experiments reported in this application were supported in part by: the National institute of General Medical Sciences, grant no. GM-29554; the National Science Foundation, grant nos. DMI-0210844, EIA-0086015, CCF-0432009, CCF-0523290 and CTS-0103002; and Army Research Office, grant no. 48681-EL. The U.S. Government has a paid-up license in this invention and the right in limited circumstances to require the patent owner to license others on reasonable terms as provided for by the terms of the above grants.

BACKGROUND OF THE INVENTION

1. Field of the Invention

The present invention relates to polynucleic acid nanostructures and lattices.

2. Description of the Related Art

Previous motifs used to design 2D crystalline arrays have included the double crossover (DX) (Fu et al., 1993; Winfree et al., 1998), triple crossover (TX) (LaBean et al., 2000), the DNA parallelogram (Mao et al., 1999), and the four-by-four structure (Yan et al., 2003). These motifs have been used to produce 2D crystalline arrays lacking symmetry or with two-fold symmetry (Seeman, 2003).

Metallic and semiconductor nanoparticles exhibit quantized optical and electronic properties that might be exploited in the design of future nanoelectronic devices (Alivisatos et al., 1996; Redl et al., 2003; Kiehl, 2000; and Likharev et al., 2003; Maier et al., 2001; and Shipway et al., 2000). However, this use requires the deliberate and precise organization of nanoparticles into specific designed structural arrangements. The control of the structure of matter on the finest possible scale entails the successful design of both stiff intramolecular motifs and robust intermolecular interactions. The specificity of DNA base-pairing has provided a 'smart-glue' approach to programming interactions between particles via hybridization of specifically designed linker strands (Alvisatos et al., 1996; Loweth et al., 1999; Zanchet et al., 2001 and 2002; Mucic et al., 1996; Storhoff et al., 1998; Jin et al., 2003; and Anderson et al., 2005). Previously, stiff motifs (Li et al., 1996; and Sa-Ardyen et al., 2003) based on branched DNA have been used to produce DNA structures with a variety of patterns that are visible in the AFM; these include stripes from DX molecules (Winfree et al., 1998), arrays with tunable cavities from DNA parallelograms (Mao et al., 1999), and honeycombs from DX triangles (Ding et al., 2004). DNA-functionalized 1.4 nm gold nanoparticles have been assembled into linear arrays forming parallel stripes on a 2D DNA striped scaffolding by self-assembly during scaffolding formation (Xiao et al., 2002) and 6 nm gold nanoparticles with multiple DNA attachments have been fashioned into similar arrays by in situ hybridization to a pre-assembled scaffolding on a striped DX surface (Le et al., 2004). Sequence-encoded in situ assembly of 5 nm and 10 nm gold particles in alternating stripes has also been achieved (Pinto et al., 2005). While such linear nanoparticle arrays are of interest for some applications, other periodic arrangements also offer significant potential. Furthermore, a more precise control over nanoparticle positions than that afforded by polyvalent functionalization is highly desirable.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

The present invention provides a two dimensional polynucleic acid array of polygonal units linked together by complementary double cohesive ends. Each of the polygonal units has, as edges, connected nucleic acid multi-crossover domains, but at least two edges of each polygonal unit have ends with two parallel double helices, where each of the two parallel double helices terminate in a cohesive end to provide a double cohesive end at each of the two edges. A double cohesive end of one edge of a polygonal unit is cohered (joined) to a complementary double cohesive end of an adjacent polygonal unit in the array to form an extended edge linking together two adjacent polygonal units. The linking together of adjacent polygonal units by complementary double cohesion of cohesive ends extends the array in two dimensions.

At least one edge of each polygonal unit in the subset of polygonal units in the array, which edge is different from the edges that terminate in double cohesive ends, has one or both ends attached to a nanoparticle or pendant molecule.

BRIEF DESCRIPTION OF THE DRAWINGS

FIG. 3A is a schematic showing the formation of a two-component array. Four triangles of two species are shown to be connected. The view parallel to the three-fold axes shows how only two domains are involved in the array formation, while the end of the third domain is free to be involved in scaffolding operations. FIG. 3B are schematic diagrams showing the attachment of nanoparticles. This view is perpendicular to the rhombic surfaces of the 2D array. Its three panels show, top to bottom, 5 nm particles attached to only one of the two tiles, 5 nm particles attached to both of the tiles, and 5 nm particles attached to one of the tiles and 10 nm particles attached to the other tile. FIG. 3C is a tapping-mode atomic force micrograph of an underivatized array. Note that despite a pseudo-trigonal appearance, the features in the lighter portion of the array are all parallel to each other, and there is no threefold axis at the centers of the triangles, nor at their vertices. There is a prominent high feature in the lower-left-to-upper-right direction that the present inventors interpret as the domain not involved in lattice formation.

FIG. 6A shows an array where one tile contains 5 nm particles. It is clear that this arrangement results in one short distance and one long distance. Sometimes a particle is missing. FIG. 6B shows an array where both tiles contain 5 nm particles. The distances between particles are seen to be equal here. FIG. 6C shows an array where one tile contains a 5 nm particle and the other tile contains a 10 nm particle. The alternation of 5 nm particles and 10 nm particles is evident from this image. Note that the spacings are precise in both directions, and that the pattern mimics the rhombic pattern of the tile array.

FIGS. 7A-7C show illustrations of a skewed TX-DX triangle. One side of the skewed TX-DX triangle is shown in FIG. 7A. It is clearly made of a pair of DX ends fused by the TX motif at the center. FIG. 7B has one side (closest to the reader) in a similar orientation as in FIG. 7A, but the other two sides have been added, including one side viewed edge on. It is evident that this motif spans 3-space. FIG. 7C is a top view of this trigonal motif.

FIGS. 8A-8C are Atomic Force Microscopy (AFM) images of three sets of two dimensional arrays of the skewed TX-DX triangle motif shown above in FIGS. 7A-7C.

FIGS. 9A-9B show illustrations of a six-helix bundle down its central axis (FIG. 9A) and along its side (FIG. 9B). FIG. 9C is a two dimensional array (lattice) viewed down the helical axes of the six-helix bundles.

FIGS. 10A and 10B are schematic illustrations of an array of six-helix bundles viewed down the helical axes (FIG. 10A) and as a perspective view (FIG. 10B), with the small and large shaded circles representing two different sized nanoparticles or pendant molecules attached to different six-helix bundles.

DETAILED DESCRIPTION OF THE INVENTION

The two dimensional polynucleic acid array according to the present invention is composed of polygonal units linked together by complementary double cohesive ends via double cohesion, where a subset of the polygonal units in the array have a nanoparticle or a pendant molecule attached to each polygonal unit of the subset. A plurality of nucleic acid multi-crossover molecules, which form each polygonal unit (a robust nucleic acid motif), such as a nucleic acid triangle motif, are assembled from single stranded oligonucleotides or polynucleotides to produce the polygonal units. Similarly, two dimensional polynucleic acid periodic arrays (lattices) are assembled from basic polygonal units of linked multi-crossover molecules.

The term "robust" as used herein is meant to refer to producing the designed structure exclusively, and no others. This applies not only to motifs but also to structures such as arrays and lattices. For instance, if a double crossover (DX) triangle is designed, then its component strands will only self-assembled into the designed DX triangle motif/structure.

DNA molecules containing two crossover sites between helical domains have been widely suggested as intermediates in recombination processes involving double stranded breaks. Accordingly, "double crossover molecules" are those nucleic acid molecules containing two branched junctions (Holliday junctions corresponding to the crossover sites) linked together by ligating two of their double helical arms. By branched junction is meant a point from which three or more helices (arms) radiate.

There are five isomers of double crossover molecules (Fu et al., 1993), which fall into two broad classes of molecules differentiated by the relative orientations, parallel (DP) or antiparallel (DA), of their helix axes. As parallel double helical molecules are usually not well behaved, antiparallel isomers of double crossover molecules are the preferred building block components intended to be used in the present invention. However, parallel double helical molecules may be suitable as well.

Figure 1A:
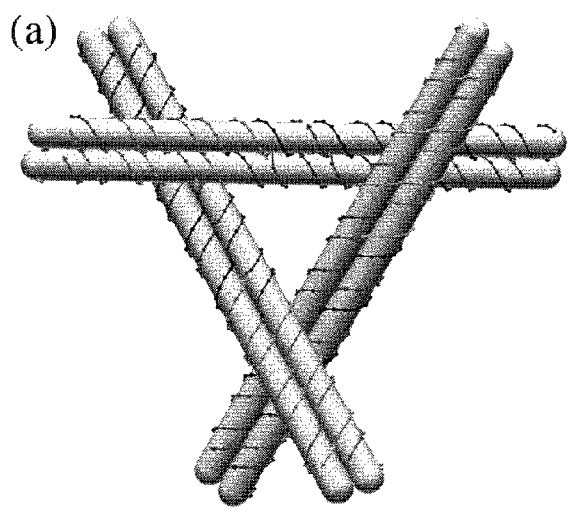
FIGS. 1A and 1B illustrate the 3D-DX triangle motif used to build the arrays constructed in the Example. In the schematic diagram of the motif shown in FIG. 1A, double helices are shown as opaque rods around which the individual strands are wrapped. Note the 3-space spanning character of the three DX domains. In the detailed molecular structure shown in FIG. 1B, each nucleotide is shown in a representation that illustrates a backbone virtual atom connected to its neighbors along the helix.
Figure 1B:
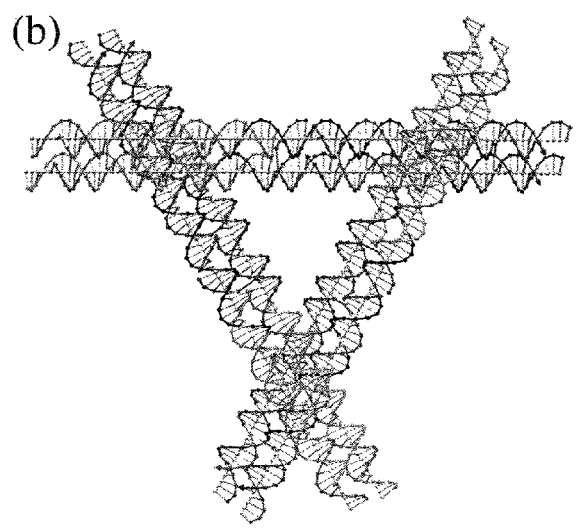

The present inventors have now developed two motifs, the 3D-DX triangle (FIGS. 1A and 1B) and the skewed TX-DX triangle (FIGS. 7A-7C), which are capable of forming a two dimensional array. The DX molecule has been shown to be about twice as stiff as conventional linear duplex DNA (Li et al., 2002; Sa-Ardyen et al., 2003). Thus, one might expect that this doubly-thick triangle would be more rigid than the simple bulged junction triangle. The self-assembly of an array from the 3D-DX triangle motif is shown in the Example hereinbelow.

Figure 3A:
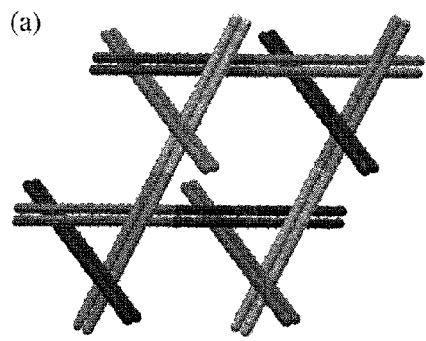
FIGS. 3A-3C show the 2D arrays assembled in this study.

Arrays or lattices formed from this 3D-DX triangle motif mentioned above and disclosed in the Example hereinbelow are preferred embodiments of the two dimensional array of the present invention. It is intended that the polynucleic acid structure of the present invention encompass not only 3D-DX triangle motifs forming arrays/lattices, i.e., rhombic array/lattice arrangement as shown in FIG. 3A but also other multi-crossover motifs, such as, but not limited to, a skewed TX-DX triangle and a six helix bundle.

A polygon as used herein is a closed geometrical structure having three or more edges or sides. While a polygon is generally thought to be confined to a plane, it is intended for the purposes of the present invention that a "polygonal unit" include motifs such as the three dimensional DX triangle (FIGS. 1A and 1B), the skewed TX-DX triangle (FIGS. 7A-7C), and the DX parallelograms presented in Constantinou et al. (2006), which are polygonal when viewed from above the motif, such as in FIGS. 1A-1B and FIG. 7C and the six helix bundle (FIGS. 9A-9C), which is polygonal when viewed down the axes of the helices. Thus, two dimensions of the monomeric unit in the array filling 3D space forms a polygon.

The polynucleic acid array of the present invention is considered to be two dimensional because the monomeric polygonal units are extended in only two dimensions and so the array appears as a two dimensional "fabric" or "mesh" in atomic force microscopy images (FIG. 3C, FIGS. 8A-8C, and FIGS. 12A-12E).

When a polygonal unit has nucleic acid multi-crossover molecules as sides of a polygon, such as in the 3D-DX triangle or in the skewed TX-DX triangle, its edges are the edges (sides) of a polygon. However, when the polygonal unit is a polygonal cylinder, then the edges are parallel to the axis of the polygonal cylinder from each corner of the polygonal face at one end of the cylinder to the corresponding corner at the other end of the cylinder. Each polygonal unit in the two dimensional polynucleic acid array of the present invention has, as its edges, connected nucleic acid multi-crossover domains. In the case of a polygonal unit such as the 3D-DX triangle, its edges are the sides of the triangle. For a polygonal cylinder, its edges are not intended to be the sides of a polygonal face of the cylinder but rather are intended to be those edges which are parallel to the axis of the cylinder as discussed above.

As would be recognized and appreciated by those of skill in the art, although the edges of each polygonal unit may be described as being formed by one or more nucleic acid multi-crossover molecule, it may not be possible to identify the discrete limits of individual nucleic acid multi-crossover molecules; rather, it may be more appropriate to think of connected nucleic acid multi-crossover domains forming the edges of a polygonal unit. This is more consistent with the manner in which polynucleic acid structures are produced according to the present invention, where individual nucleic acid strands self-assemble to form a polygonal unit based on sequence complementarity. Accordingly, the edges are not formed as individual molecules to be linked together but rather are self-assembled as a whole into a polygonal unit.

At least two edges of each of the polygonal units in the array have two ends with two parallel nucleic acid double helices. Each of the at least two parallel nucleic acid double helices terminate in a cohesive or sticky end. The double cohesive ends can be the same or different cohesive ends. A double cohesive end of one edge of a polygonal unit is cohered to a complementary double cohesive end of an adjacent polygonal unit.

The nucleic acid multi-crossover domains preferably can be double or triple crossover domains or a combination thereof, such as exemplified by the skewed TX-DX triangle shown in FIGS. 7A-7C.

The polygonal unit can be any which can be suitably extended from two or more of its edges to join other polygonal units and form an array or lattice. Preferably, the polygonal unit is a triangle or a six helix bundle, although it is not limited to such.

A preferred embodiment of the two dimensional polynucleic acid array of the present invention is an array of triangular units linked together by complementary double cohesive ends to form a rhombic array/lattice arrangement. More preferably, the array is a rhombic array of two or more different triangular units. Another preferred embodiment is an array of six helix bundle units linked by complementary double cohesive ends. Similarly, this array preferably has two or more different six helix bundle polygonal units. FIGS. 10A-10B and 11A-11B exemplify arrays of six helix bundles which can be composed of one or more different six helix bundle polygonal units. Tiling with different species of tiles are taught in U.S. Pat. No. 6,255,469 with reference to the mathematical theory of tiling (Grunbaum et al., 1986), rectangular tiles with programmable interactions, known as Wang tiles (Wang, 1963), and double crossover molecules acting as molecular Wang tiles to self assemble and perform desired computations (Winfree, 1996), the contents of which are incorporated by reference in regards to tiling.

A nanoparticle and/or a pendant molecule is attached to at least one edge of each polygonal unit in a subset of polygonal units in the array (which edge is different from the at least two edges of a polygonal unit that are involved in linking together adjacent polygonal units by double cohesion). This at least one edge has one or both of its ends attached to a nanoparticle or pendant molecule. The nanoparticle is preferably, but not limited to, gold (Au) or CdSe. It can be nanoparticles of metallic clusters (i.e., silver clusters; Alivisatos et al., 1996; Mirkin et al., 1996; Brann et al., 1998), semi-conductors, or magnetic material, etc. The pendant molecule can be small molecules, catalysts, enzymes, peptides and other proteins, i.e., ribosomes, (Niemeyer et al., 1994). WO 95/34890 discloses multiple chromphoric memory units for photo-write operation. The two dimensional polynucleic acid arrays of the present invention with attached chromophoric memory units can provide such photo-write operation.

As will be appreciated by one of skill in the art, there can be two or more different nanoparticles and/or pendant molecules that are attached to the polygonal units in the subset of polygonal units in the array. The difference in the attached nanoparticles and/or pendant molecules can be in composition or merely in size. The placement of nanoparticles and/or pendant molecules in the array can be periodic or aperiodic. In addition, the attached nanoparticles and/or pendant molecules can be disposed above or below the plane of the two dimensional polynucleic acid array or both. FIGS. 10A-10B and 11A-11B show two dimensional arrays of six helix bundles with different attached nanoparticles and/or pendant molecules disposed above and below the plane of the array.

The polygonal units, with or without a nanoparticle or a pendant molecule, are self-assembled, which self assembly involves synthesizing single stranded polynucleotides, each being designed to be self-complementary and/or complementary to another single stranded polynucleotide so as to be able to self anneal into a polygonal unit; mixing the single stranded polynucleotides to form a mixture of polynucleotides; heat denaturing the mixture; and annealing the heat denatured mixture of single stranded polynucleotides to form the polygonal unit.

Single stranded polypeptides are mixed together and heated at a temperature above the melting temperature or denaturation temperature of the complementary strands, e.g., 90° C., to eliminate any initial secondary structures present in the mixture, and then cooled slowly to allow the strands to anneal based on sequence complementarity.

Once the individual polygonal units are self-assembled, the assembled polygonal units can form arrays and lattices based on joining of double cohesive ends on polygonal units. The self-assembled, polygonal units are first heated to ensure that the double cohesive ends are exposed, and then the exposed double cohesive ends that are complementary are annealed to form an array of polygonal units. More than one polygonal unit, such as different polygonal units, can be mixed to form an array of different polygonal units.

It should also be understood that when synthesizing the single stranded oligonucleotides or polynucleotides for forming the topologically closed nucleic acid structure, the choice of sequence is substantially arbitrary, provided that strands intended to form a hairpin or to be opposite one another are complementary. It is preferable to use previously described symmetry minimization algorithms (Seeman, 1990; Seeman, 1981 and 1982) in order to optimize the sequences and incorporate the desired features while avoiding unwanted cross-hybridization or branch migration.

It should also be appreciated that the term "nucleic acid" refers to both DNA and RNA and hybrids of the two. The structure need not resemble anything which can theoretically be made from nature. For example, one or more strands may contain PNA or other backbone molecules (Lukeman et al., 2004). A particular oligonucleotide or polynucleotide strand may employ bases other than the standard five, adenine, cytosine, guanine, thymine and uracil. Derivatized (e.g., methylated) and other unusual bases such as iso-guanine, iso-cytosine, amino-adenine, K, X, n, (Piccirilli et al., 1990), inosine and other derivatives of purine and pyrimidine may be used. A preferable feature in the selection of the bases is that they be capable of interacting with a base opposing them to form a specifically paired attraction. In natural DNA and RNA, hydrogen bonding forms this interaction. However, opposite ion charges, hydrophobic interactions and van der Waals forces may also be acceptable forms of interaction. These interactions expand the choices over naturally occurring bases to give a wider assortment of physical properties.

Within a particular strand, the heterocyclic base may be entirely missing from the sugar moiety. This may be particularly desirable where the strands bend, form a junction, or where one desires fewer forces holding the strands together.

A particular strand need not have a single contiguous ribose-phosphate or deoxyribose-phosphate backbone. It could be a peptide nucleic acid with a peptide backbone. One may employ a simple inorganic or organic moiety or polymeric spacer between segments of polynucleotide. Spacers such as polyethylene, polyvinyl polymers, polypropylene, polyethylene glycol, polystyrene, polypeptides (enzymes, antibodies, etc.) peptide nucleic acids (PNA), polysaccharides (starches, cellulose, etc.) silicones, silanes and copolymers, etc., may be employed. An example of such a hybrid structure is dodecadiol having phophoramidite at one end. This structure has been inserted covalently instead of four T nucleotides to form a hairpin loop in a fashion similar to the nucleotides it replaces. See Mitchel J. Doktycz, Ph.D. Thesis (1991), University of Illinois, Chicago. The term "oligonucleotide", "polynucleotide" and "nucleic acid" are intended to cover all of these structures.

In nature and in the field of molecular biology, double stranded DNA generally occurs in the B form. However, for the purposes of this invention it may be desirable for DNA or other double stranded polynucleotide to exist in the A, C, D or Z form. Various bases, derivations and modifications may be used to stabilize the structure in the A, C, D or Z form as well.

The two dimensional polynucleic acid array of the present invention have numerous uses. Because of the minute size of the array and its polygonal units, it has application in the field of nanotechnology, particularly nanoelectronics, where conductors, semi-conductors and/or magnetic particles are attached to polygonal units as nanoparticles.

The two dimensional polynucleic acid array also has utility in protein or enzyme immobilization technology. Conventional enzyme immobilization techniques depend on random attachment and thus the solid phase particles formed are not uniform in either activity or structure. By contrast, one can attach a predetermined number of enzymes to the polynucleotide strands being added to form a structure with a fixed number and orientation of enzymes.

The two dimensional polynucleic acid array of the present invention can also create a mesh or screen-like material. This material can be used as a filter of very precise porosity. For added strength, plural layers of mesh may be linked together or a layer may be bound to any other conventional substrate.

Having now generally described the invention, the same will be more readily understood through reference to the following example which is provided by way of illustration and is not intended to be limiting of the present invention.

EXAMPLE

2D Nanoparticle Arrays Generated from Two 3D-DX Motifs

Materials and Methods

Figures 2A, 2B:
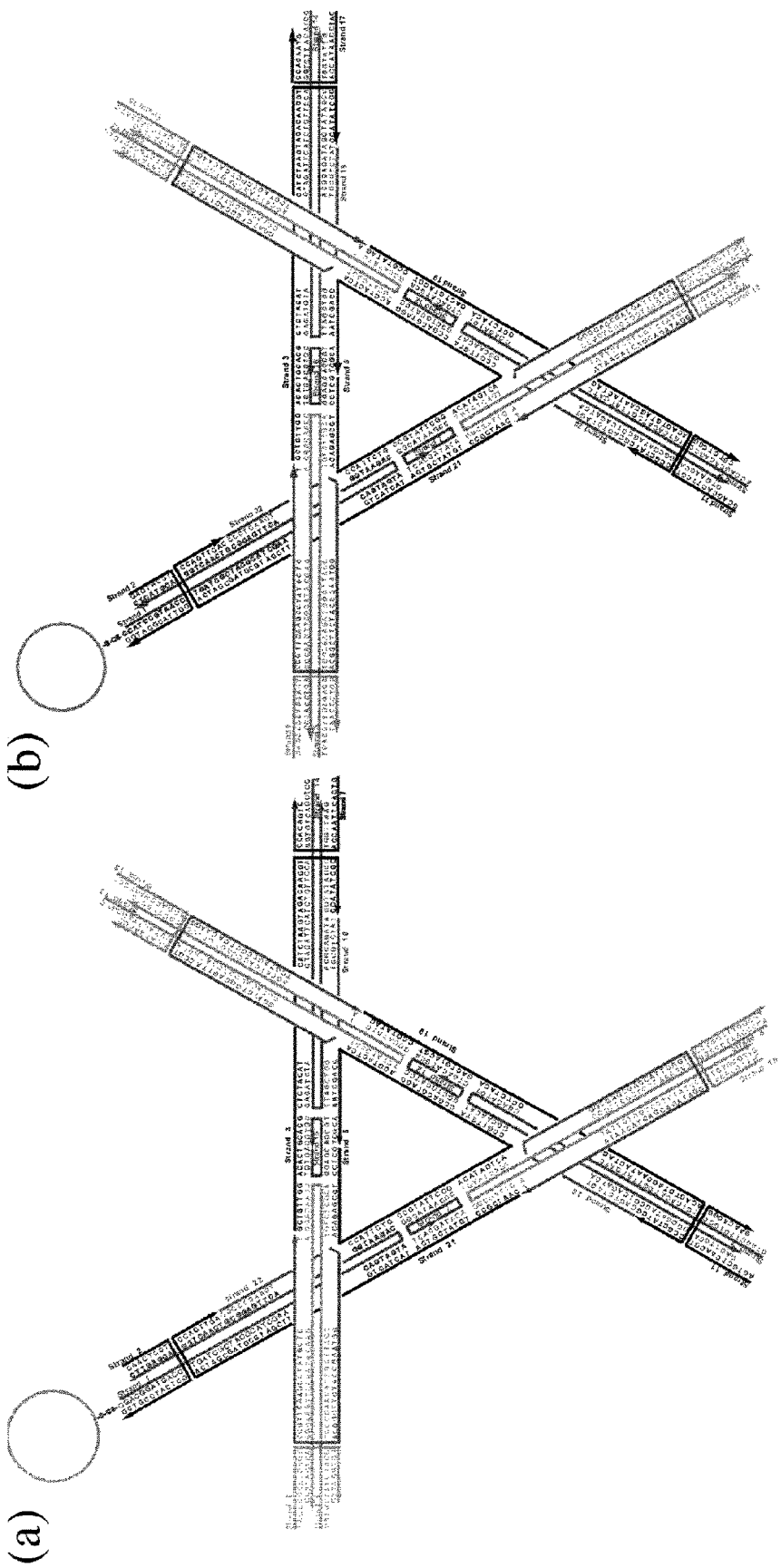
FIGS. 2A and 2B schematically show the arrangement and nucleotide sequences of the 3D-DX triangle motifs DXT-A (FIG. 2A; SEQ ID NOs: 1-22) and DXT-B (FIG. 2B; SEQ ID NOs: 23-44). The helices have been unwound with the thiol attached gold nanoparticles being shown as a circle. The 3' ends are indicated by arrowheads.

DNA sequences were designed using SEQUIN (Seeman, 1990), were synthesized by standard phorphoramidite techniques (Caruthers, 1985) and purified from denaturing polyacrylamide gels. 3D-DX triangle DNA molecules and their 2D assembly were constructed by annealing stoichiometric mixtures of the strands (estimated by $OD_{260}$) to a concentration of 0.5 μM in a buffer solution containing 10 mM HEPES, 1 mM EDTA, 3.5 mM $MgCl_2$ and 100 mM NaCl from 90° C. to room temperature. The strands and sequences used for assembly of the two 3D-DX triangles, DXT-A and DXT-B, in FIGS. 2A and 2B are presented below in Table 1.

TABLE 1

Strand and Sequences for 3D-DX Triangles (DXT) Used To Generate 2D Nanoparticle Arrays

DXT-A

STRAND 1 (72 bases) 5' thiol modification
CGACGGATGACCTGATCGCTACGCATCGAACAGTAGT   SEQ ID NO:1
ACAGAATGGACTTGAGGCGTCAACTGGACGAGTTC STRAND 2 (20 bases)
GAACTCGTGGTCATCCGTCG                    SEQ ID NO:2

STRAND 3 (53 bases)
GCTGTTGGACACTGCACGCTCTACATCATCTAAGTAG   SEQ ID NO:3
ACAAGGTGGCTATACC STRAND 4 (76 bases)
GATGCAATCTACCTGCCGAAGATGGCTTACCTGTCTC   SEQ ID NO:4
GCACCAACAGCAGAGCATAGGCTTGAACGGACTCATG
CG STRAND 5 (81 bases)
GCTCCTGCGAGACACCATTCTGCCGTATTCGGACATA   SEQ ID NO:5
GTCACCGTTGTACCGACGTAGGACGTACTCACCAGCT
AAACGCT STRAND 6 (22 bases)
TAGCCGCATGAGTGGTAGATTG                  SEQ ID NO:6

STRAND 7 (20 bases)
ATACACCGAATACGGTCACG                    SEQ ID NO:7

STRAND 8 (76 bases)
ACGCCAATCCAGGACTGAATCGTCGCTCGCCTGACTA   SEQ ID NO:8
TGTGGCGATTGATATTGTAGTCGTCTATCCTGTGCGT
TG STRAND 9 (72 bases)
GTAGCTTGTGCCTGTCACATCGTTATGATCCGAGATG   SEQ ID NO:9
TTACAACGGACTAGACTGCGATAGCGGACGTTGAG STRAND 10 (22 bases)
CAACGCACACCTGGATTGGCGT                  SEQ ID NO:10

STRAND 11 (20 bases)
AGTGCTCAACGTGGCACAAG                    SEQ ID NO:11

TABLE 1-continued

Strand and Sequences for 3D-DX Triangles (DXT) Used To Generate 2D Nanoparticle Arrays STRAND 12 (20 bases)
ATGCACCTACGTCGGCTGAC                               SEQ ID NO:12

STRAND 13 (76 bases)
CTGCGGTTCATGGACGGTAACTGCCAGATCCTGAGTA              SEQ ID NO:13
CGTGGCATATCTAGCATCAGCGAGTGTTCCTGCTTGC
TC STRAND 14 (72 bases)
GCTCGACTGTGGACCTTGTCTACTTAGATGATGTAGA              SEQ ID NO:14
GTTAGCTGGACGCAGATAGGTATAGCCTGGTTAAG STRAND 15 (22 bases)
TCGTGAGCAAGCACCATGAACC                             SEQ ID NO:15

STRAND 16 (20 bases)
AGTGTGGAGCAGCGTCGTGC                               SEQ ID NO:16

STRAND 17 (20 bases)
GTCACTTAACCACCACAGTC                               SEQ ID NO:17

STRAND 18 (46 bases)
TATCTGCGTGGATCTGGCAGTTACCGTGGAACACTCG              SEQ ID NO:18
CTGATGCTA STRAND 19 (53 bases)
GATATGCCTGCATGTCAGACATCTCGGATCATAACGA              SEQ ID NO:19
TGTGACACCGCTATCG STRAND 20 (46 bases)
CAGTCTAGTGGCGAGCGACGATTCAGTGGATAGACGA              SEQ ID NO:20
CTACAATAT STRAND 21 (53 bases)
CAATCGCCTGTATCGTGATACTACTGTTCGATGCGTA              SEQ ID NO:21
GCGATCACCAGTTGAC STRAND 22 (46 bases)
GCCTCAAGTGGTAAGCCATCTTCGGCACCGTTCAAGC              SEQ ID NO:22
CTATGCTCT

DXT-B

STRAND 1 (72 bases) 5' thiol modification
CCATCCGTAACCTGATCGCTACGCATCGAACAGTAGT              SEQ ID NO:23
ACAGAATGGACTTGAGGCGTCAACTGGACGTACTC STRAND 2 (20 bases)
GAGTACGTGGTTACGGATGG                               SEQ ID NO:24

STRAND 3 (53 bases)
GCTGTTGGACACTGCACGCTCTACATCATCTAAGTAG              SEQ ID NO:25
ACAAGGTGGCTATACC STRAND 4 (76 bases)
TGACGTTGCGACCTGCCGAAGATGGCTTACCTGTCTC              SEQ ID NO:26
GCACCAACAGCAGAGCATAGGCTTGAACGGACTCCAG
CG STRAND 5 (81 bases)
GCTCCTGCGAGACACCATTCTGCCGTATTCGGACATA              SEQ ID NO:27
GTCACCGTTGTACCGACGTAGGACGTACTCACCAGCT
AAACGCT STRAND 6 (22 bases)
GAGCCGCTGGAGTGGTCGCAAC                             SEQ ID NO:28

STRAND 7 (20 bases)
ATACACCGAATACGGTCACG                               SEQ ID NO:29

STRAND 8 (76 bases)
AGCAACCGCCAGGACTGAATCGTCGCTCGCCTGACTA              SEQ ID NO:30
TGTGGCGATTGATATTGTAGTCGTCTATCCTGTGAAG
CT

TABLE 1-continued

Strand and Sequences for 3D-DX Triangles (DXT) Used To Generate 2D Nanoparticle Arrays STRAND 9 (72 bases)
ACGAGCACAGCCTGTCACATCGTTATGATCCGAGATG              SEQ ID NO:31
TTACAACGGACTAGACTGCGATAGCGGACGAAGTG STRAND 10 (22 bases)
AGCTTCACACCTGGCGGTTGCT                             SEQ ID NO:32

STRAND 11 (20 bases)
GCAGCACTTCGTGGCTGTGC                               SEQ ID NO:33

STRAND 12 (20 bases)
ATGCACCTACGTCGGCTGAC                               SEQ ID NO:34

STRAND 13 (76 bases)
CACTGTCGTATGGACGGTAACTGCCAGATCCTGAGTA              SEQ ID NO:35
CGTGGCATATCTAGCATCAGCGAGTGTTCCTGCTACC
TC STRAND 14 (72 bases)
GCTACTCTGTGGACCTTGTCTACTTAGATGATGTAGA              SEQ ID NO:36
GTTAGCTGGACGCAGATAGGTATAGCCTGGTATTG STRAND 15 (22 bases)
CTACGAGGTAGCACCATACGAC                             SEQ ID NO:37

STRAND 16 (20 bases)
AGTGTGGAGCAGCGTCGTGC                               SEQ ID NO:38

STRAND 17 (20 bases)
CATCCAATACCACCACAGAG                               SEQ ID NO:39

STRAND 18 (46 bases)
TATCTGCGTGGATCTGGCAGTTACCGTGGAACACTCG              SEQ ID NO:40
CTGATGCTA STRAND 19 (53 bases)
GATATGCCTGCATGTCAGACATCTCGGATCATAACGA              SEQ ID NO:41
TGTGACACCGCTATCG STRAND 20 (46 bases)
CAGTCTAGTGGCGAGCGACGATTCAGTGGATAGACGA              SEQ ID NO:42
CTACAATAT STRAND 21 (53 bases)
CAATCGCCTGTATCGTGATACTACTGTTCGATGCGTA              SEQ ID NO:43
GCGATCACCAGTTGAC STRAND 22 (46 bases)
GCCTCAAGTGGTAAGCCATCTTCGGCACCGTTCAAGC              SEQ ID NO:44
CTATGCTCT Gold colloids with mean diameters of 5 and 10 nm were purchased (Ted Pella). Citrate-stabilized gold colloids were subsequently passivated with a monolayer of anionic phosphine molecules as described elsewhere (Zanchet et al., 2001 and 2002). The colloidal solution was concentrated up to the micromolar range after phosphine coating. ssDNA/Au conjugates were prepared by mixing gold (Au) nanoparticles with 5'-thiolated (—SH) ssDNA in a mole ratio of 3:1 and incubated for 2 h in a buffer containing 10 mM HEPES, 1 mM EDTA and 50 mM NaCl (HEPES buffer). The Au nanoparticles tethered with single DNA strands were purified by gel electrophoresis (3% agarose gel at 5V/cm, HEPES buffer 10 mM HEPES, 1 mM EDTA), and then recovered by cutting and extracting the appropriate band (Zanchet et al., 2001 and 2002). ~100 uL red-color solution was collected and then diluted to a final volume of 500 μL in a solution containing 100 mM Na and HEPES buffer. After further incubation for 5 h the volume was slowly reduced to 100 μL by vacuum centrifugation at room temperature. This process produces a gradual increase in ionic strength, which leads to much more stable DNA/Au conjugates.

The 3D-DX Triangle DNA/Au conjugate was prepared by mixing the ssDNA-Au strands and other 21 component DNA strands in HEPES buffer for overnight annealing from 75° C. to room temperature. The final reaction volume was 50 µL and the concentration of each oligonucleotide was 0.5 µM, except for the Au/DNA conjugates, which were present at 0.8 µM. The 3D-DX triangle DNA/Au conjugates were purified and collected following the same procedure as above.

To form the array, the two conjugates were mixed in stoichiometric quantities, warmed to 45° C., and cooled slowly to room temperature in a 2 L water bath in a Styrofoam box over 24 h. The low initial temperature was used to ensure the stability of Au/DNA conjugate. Following this incubation, visualization of the particles was carried out by transmission electron microscope (TEM).

TEM imaging was performed using a Philips CM-10 instrument operated at 80 kV. The particle sample was prepared on 400 mesh formvar-coated copper grids by dropping 5 µL sample solution on grids and then wicking off excess solution using filter paper after 30 s. All grids were dried in a desiccator at least overnight.

Results and Discussion

The experience in the laboratory of the present inventors with honeycomb lattices demonstrates that cohesion by two sticky ends on each end of a DX molecule is more robust than a single sticky end. The laboratory of the present inventor was unable to obtain the honeycomb arrays if only a single sticky end was used (Ding et al., 2004). However, several motifs that span 3-space (e.g., 6-helix bundles; Mathieu et al., 2005) were built; one of these motifs (termed a 3D-DX triangle) is based on Mao's tensegrity triangle (Liu et al., 2004), but contains DX molecules (FIGS. 1A and 1B), instead of single helices in each of its three domains. It is possible to produce 2D lattices with this motif if only two of the linearly independent directions contain cohesive ends. This leaves a third direction not involved in lattice formation, and its blunt end can be used as a site to include a gold nanoparticle. Specificity is increased by using a nanoparticle that contains only a single DNA strand; this strand is one of the strands that form the motif and its 5' end is on one of the blunt ends. Thus, the present inventors have developed a system that combines all of the robustness features of which the present inventors are aware, single-stranded attachment of the nanoparticle, DX-cohesion and a 3-space-spanning triangular motif based on stiff DX molecules. To demonstrate the organizational power of this system, the nanoparticles were attached to single 3D-DX triangles, as well as to a mixed system with two different tiles, to produce a well-positioned alternating 2D array of 5 nm and 10 nm gold nanoparticles.

Figure 4:
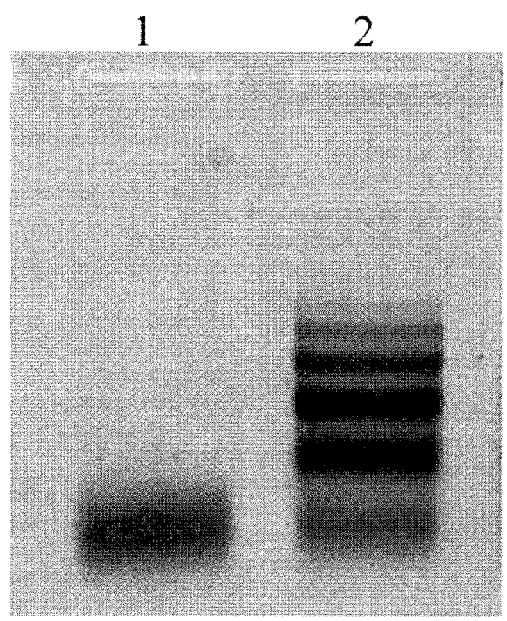
FIG. 4 is a 3% agarose gel showing the purification of nanoparticles attached to a single DNA strand. Lane 1 contains 5 nm gold particles and lane 2 contains a crude preparation of 5 nm nanoparticles to which the thiolated DNA strand of the 3D-DX triangle has been attached.
Figure 5:
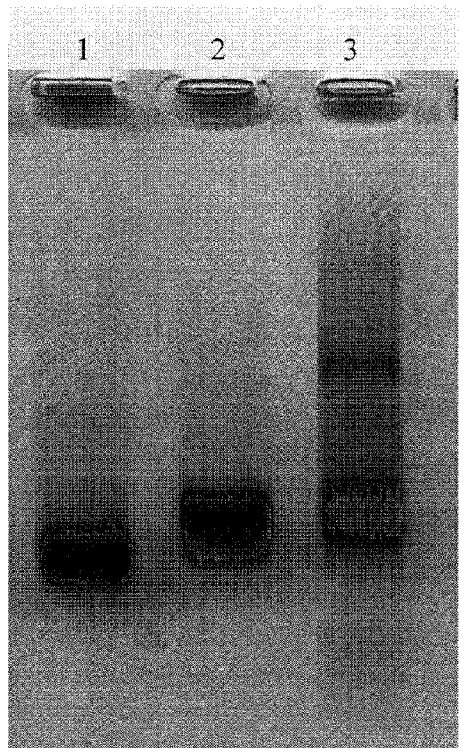
FIG. 5 is a 2.5% agarose gel showing the purification of a 3D-DX triangle containing a single gold nanoparticle. Lane 1 contains 5 nm gold nanoparticles, Lane 2 contains 5 nm gold nanoparticles derivatized with a single DNA strand, and Lane 3 contains a crude preparation of 5 nm nanoparticles to which the 3D-DX triangle has been attached. The dark band about 60% from the top contains the 3D-DX triangle attached to the gold nanoparticle.

Two 3D-DX triangles were designed to produce a rhombic lattice arrangement when combined (FIG. 3A). The sequences of the strands used to form the two triangles are shown in FIGS. 2A and 2B and listed in Table 1. The edges of triangles contain 84 nucleotide pairs (8 turns of 10.5-fold DNA, ~27.2 nm) in each of their helices, and two of the directions terminate in 5' sticky ends, four nucleotides in length. The particles are attached to the triangles following two-step electrophoretic isolation processes. In the first step, thiolated single-stranded DNA (ssDNA) is reacted directly with 5 nm or 10 nm Au nanoparticles. Discrete bands of low mobility that appear in the same lane (FIG. 4) on an agarose gel correspond to a defined number of strands per particle (Alivisatos et al., 1996; Loweth et al., 1999; Zanchet et al., 2001 and 2002). The band corresponding to nanoparticles bearing one ssDNA was isolated from the other bands, and recovered as described elsewhere (Alivisatos et al., 1996; Loweth et al., 1999; Zanchet et al., 2001 and 2002). The highly purified DNA/Au conjugates were subsequently added to the solution containing all other component strands, to form the 3D-DX triangle. The gel in FIG. 5 shows that the 3D-DX triangle/Au complex appears as a band with lower mobility. Following a similar isolation procedure, the collected 3D-DX triangle-Au conjugates were mixed with the complementary 3D-DX triangles, to form a 2-triangle array.

Figure 3B:
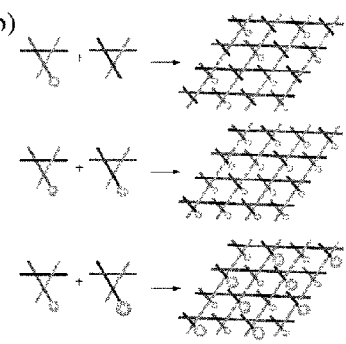
Figure 3C:
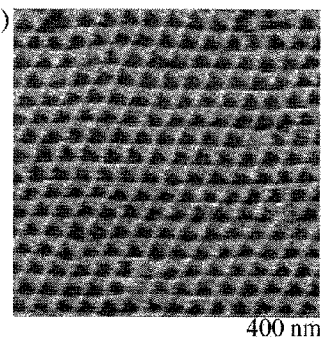

FIG. 3B contains schematics perpendicular to the 2D array, with the derivatized DX domain indicated and shown foreshortened. FIG. 3C illustrates an AFM image of an array that has not been derivatized. Although pseudo-trigonal in aspect, the parallelogram-like structure of the designed arrangements is evident from close inspection of the image. The triangle motifs can be seen to associate with each other to form the 2D lattice, with a periodic repeat of 27.4 nm (estimated from the autocorrelation function).

Figure 6A:
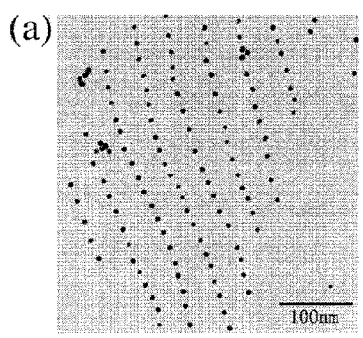
FIGS. 6A-6C are transmission electron micrographs of 2D arrays of organized gold nanoparticles.
Figure 6B:
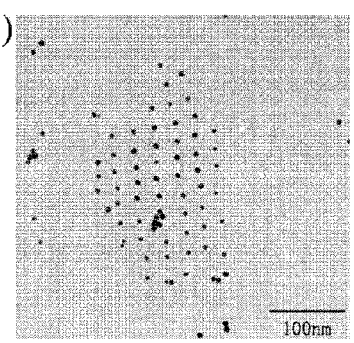
Figure 6C:
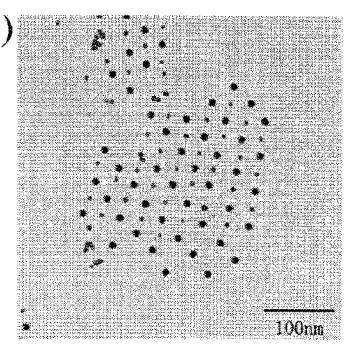
Figures 11A, 11B:
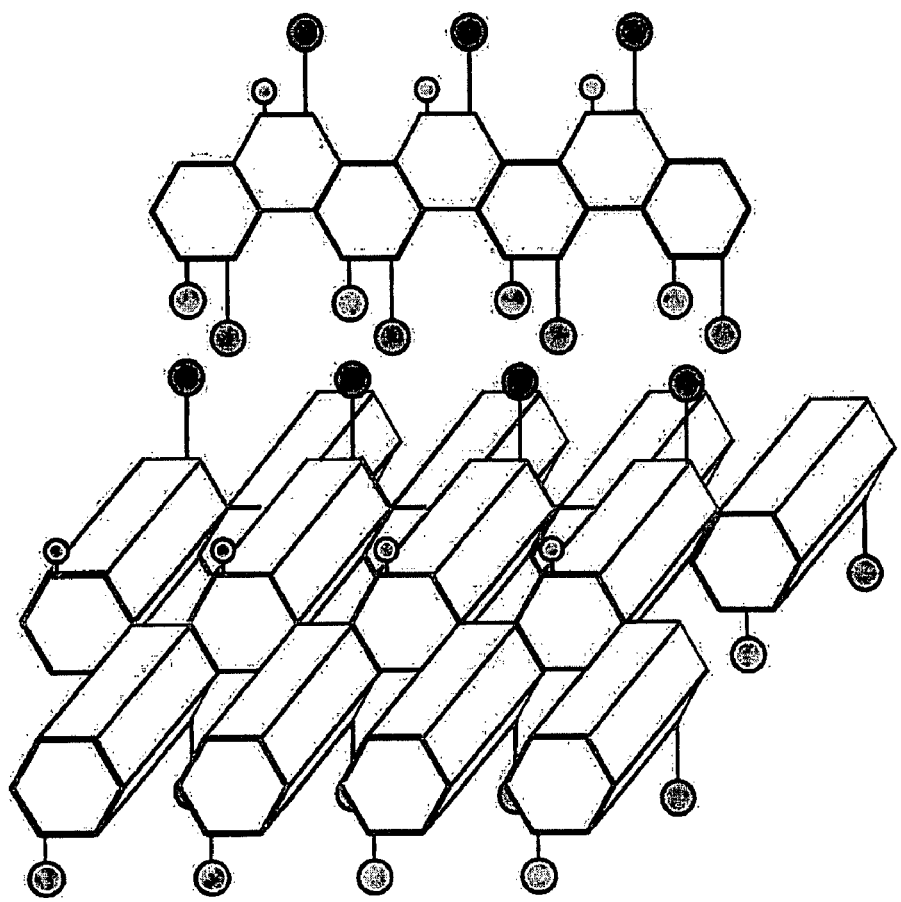
FIGS. 11A and 11B are schematic illustrations of an array of six-helix bundles viewed down the helical axes (FIG. 11A) and as a perspective view (FIG. 11B), with the shaded circles representing four different nanoparticles or pendant molecules attached to six-helix bundles. Pairs of two different nanoparticles or pendant molecules are attached to the same six-helix bundle but at opposite ends.
Figure 12A:
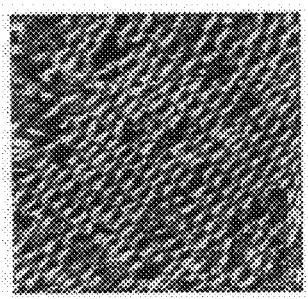
FIGS. 12A-12E are AFM images of two dimensional two tile (i.e., two different species of the six helix unit) array of six helix bundles, with FIG. 12B being an autocorrelation.
Figure 12B:
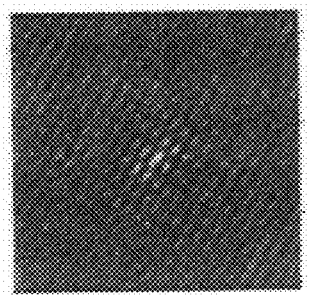
Figure 12C:
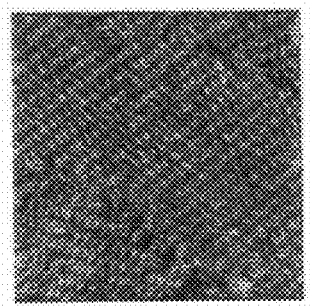
Figure 12D:
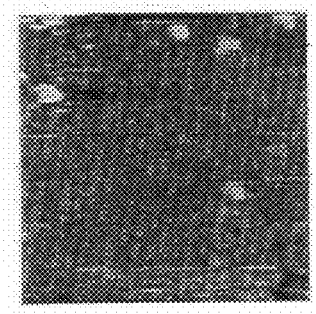
Figure 12E:
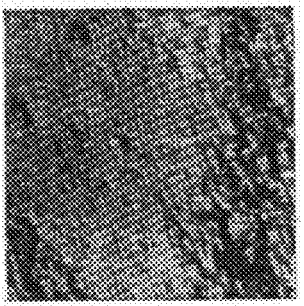
Figure 12F:
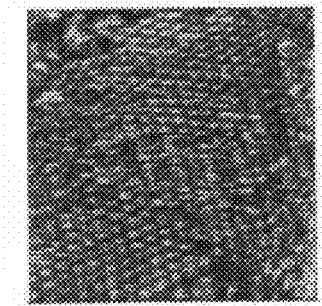

FIGS. 6A-6C show TEM images of the designs in FIG. 3B. FIG. 6A illustrates an A-B array in which the A-triangles contain 5 nm gold particles and the B-triangles do not. The spacing is twice as large in one direction as in the other. In FIG. 6B, both triangles contain 5 nm gold particles, and the spacings are the same (the short direction of FIG. 6A in both cases). In FIG. 6C, the B-triangles contain 10 nm gold particles, and the A-triangles contain 5-nm gold particles. The alternation in size with two-dimensional regularity is evident in this image. The Au nanoparticles are evenly spaced, separated on average by 27.6±0.5 nm in FIGS. 6B and 6C, and by 25.4±0.7 in the short direction while 54.9±0.9 nm in the long direction of FIG. 6A; these values are in good agreement with the expected values of 27.2 and 54.4 nm, respectively.

It is evident from these results that the combination of robust motifs, robust cohesion and specific attachment of particles makes it possible to incorporate different metallic nanoparticles into a highly precise 2D periodic pattern. It is clear that more complex periodic patterns could also be generated in 2D by using more tile species. In a similar fashion, 2D algorithmic assembly (Winfree, 1996) might be used to produce aperiodic patterns of nanoparticles. It is likely that the methods described here could be used to produce ordered 2D arrays of species smaller than those used here, such as biological macromolecules or organic molecules.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by references.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Alivisatos, A. P. *J. Phys. Chem.*, 100:13226-13239 (1996).
Alivisatos, A.; Johnsson, K.; Peng, X.; Wilson, T.; Lowth, C.; Bruchez, M. and Schultz, P. *Nature*, 382:609-611 (1996).
Anderson, C. J.; Sykes, T. J.; Kornberg, R. D. *Proc. Nat. Acad. Sci. (USA)* 102:13383-13385 (2005).
Brun, Y., Gopalkrishnan, M., Reishus, D., Shaw, B., Chelyapov, N. and Adleman, L., Building Blocks for DNA Self-Assembly, In: *Foundations of Nanoscience: Self-Assembled Architectures and Devices*, ed. by J. Reif, a Symposium at Snowbird, Utah, April 21-23, pp. 2-15, *Science Technica, Inc.* (2004)
Braun et al., DNA-templated assembly and electrode attachment of a conducting silver wire, *Nature*, 391:775-778 (1998)
Caruthers, M. H. *Science* 230:281-285 (1985).
Constantinou, P. E., Wang, T., Kopatsch, J., Israel, L. B., Zhang, X., Ding, B., Sherman, W. B., Wang, X., Zheng, J., Sha, R. and Seeman, N. C., Double Cohesion in Structural DNA Nanotechnology, *Org. Biomol. Chem.*, 4:3414-3419 (2006)
Ding, B.; Sha, R.; Seeman, N. C. *J. Am. Chem. Soc.* 126: 10230-10231 (2004).
Fu, T.-J.; Seeman, DNA Double Crossover Structures, *Biochemistry*, 32:3211-3220 (1993)
Grunbaum et al., *Tilings and Patters* (W.H. Freeman and Company, New York) 1986
Jin, R.; Wu, G.; Li, Z.; Mirkin, C.; Schatz, G. *J. Am. Chem. Soc.* 125:1643-1654 (2003).
Kappraff, J., *Connections*, McGraw-Hill, New York, 209-253 (1990)
K. K. Likharev, "Electronics Below 10 nm", in: J. Greer et al. (eds.), Nano and Giga Challenges in Microelectronics (Elsevier, Amsterdam, 2003), pp. 27-68.
Kiehl, R. A. *J. Nanopart. Res.* 2:331-332 (2000).
LaBean, T.; Yan, H.; Kopatsch, J.; Liu, F.; Winfree, E.; Reif, J. H.; Seeman, The Construction, Analysis, Ligation and Self-Assembly of DNA Triple Crossover Complexes, N. C. *J. Am. Chem. Soc.*, 122:1848-1860 (2000)
Le, J. D.; Pinto, Y.; Seeman, N. C.; Musier-Forsyth, K.; Taton, T. A.; Kiehl, R. A. Nano Lett. 4:2343-2347 (2004).
Liu, B.; Leontis, N. B.; Seeman, N. C. *Nanobiol.*, 3:177-188 (1994)
Li, X.; Yang, X.; Qi, J; Seeman, N. C. *J. Am. Chem. Soc.* 118: 6131-6140 (1996).
Li, X.; Zhan, Z.-Y. J.; Knipe, R.; Lynn, D. G., *J. Am. Chem. Soc.*, 124:746 (2002)
Liu, D.; Wang, M.; Deng, Z.; Walulu, R.; Mao, C., *J. Am Chem. Soc.* 126:2324-2325 (2004).
Loweth, C.; Caldwell, W.; Peng, X.; Alivisatos, P. and Schultz, P. *Angew. Chem., Int. Ed.* 38:11808-1812 (1999).
Lukeman, P. S.; Mittal, A.; Seeman, N. C., Two Dimensional PNA/DNA Arrays: Estimating the Helicity of Unusual Nucleic Acid Polymers, *Chemical Communications*, 2004: 1694-1695 (2004)
Ma, R.-I.; Kallenbach, N. R.; Sheardy, R. D.; Petrillo, M. L.; Seeman, N. C., 3-Arm Nucleic Acid Junctions Are Flexible, *Nucl. Acids Res.*, 14:9745-9753 (1986)
Maier, S. A.; Brongersma, M. L.; Kik, P. G.; Meltzer, S.; Requicha, A. A. G.; Atwater, H. A. *Adv. Mater.* 13:1501-1505 (2001).
Mao, C.; Sun, W.; Seeman, N. C., Designed Two-Dimensional DNA Holliday Junction Arrays Visualized by Atomic Force Microscopy, *J. Am. Chem. Soc.*, 121:5437-5443 (1999)
Mathieu, F.; Liao, S.; Mao, C.; Kopatsch, J; Wang, T.; Seeman, N. C., *NanoLett* 5:661-665 (2005).
Mirkin et al., A DNA-based method for rationally assembling nanoparticles into macroscopic materials, *Nature*, 382:607-609 (1996)
Mucic, R.; Storhoff, J.; Letsinger, R.; Mirkin, C. *Nature* 382: 607-609 (1996).
Niemeyer et al., Oligonucleotide-directed self-assembly of proteins, *Nucl. Acids Res.*, 22:5530-5539 (1994)
Piccirilli, J. A.; Krauch, T.; Moroney, S. E.; Brenner, S. A., *Nature*, 343:33-37 (1990)
Pinto, Y. Y; Le, J. D.; Seeman, N. C.; Musier-Forsyth, K.; Taton, T. A.; Kiehl, R. A., Nano Lett. 5, in press (2005).
Qi, J.; Li, X.; Yang, X.; Seeman, N. C., *J. Am. Chem. Soc.*, 118:6121-6130 (1996)
Redl, F. X.; Cho, K.-S; Murray, C. B.; O'Brien, S. *Nature* 423:978-971 (2003).
Sa-Ardyen, P.; Vologodskii A. V.; Seeman, N. C. *Biophys. J.* 84: 3829-3837 (2003).
Seeman, N. C. J. Biomol. *Str. & Dyns.* 8:573-581 (1990).
Seeman, N. C., DNA in a material world, *Nature*, 421:427-431 (2003)
Shipway, A. N.; Katz, E.; Willner, I., *Chem Phys Chem* 1:18-52 (2000).
Storhoff, J.; Elghenian, R.; Mucic, R.; Mirkin, C. *J. Am. Chem. Soc.* 120:1959-1964 (1998).
Wang, J. C., Helical repeat of DNA in solution, *Proc. Nat. Acad. Sci. USA*, 76:200-203 (1979)
Winfree E. On the computational power of DNA annealing and ligation. In *DNA Based Computing*, ed. E J Lipton, E B Baum. 199-219. Providence: Am. Math. Soc. 219 pp (1996).
Winfree, E.; Liu, F.; Wenzler, L. A.; Seeman, N. C., Design and Self-Assembly of Two-Dimensional DNA Crystals, *Nature*, 394:539 (1998)

Winfree et al., Universal computation via self-assembly of DNA: Some theory and experiments, in Proceedings of the 2*nd* DIMACS Meeeting on DNA Based Computers, held at Princeton University, Jun. 10-12, 1996 (American Mathematical Society, Providence, R. I., in press)

Xiao, S.; Liu, F.; Rosen, A.; Hainfeld, J.; Seeman, N. and Kiehl, R. J. Nanoparticle Resear. 4:313-317 (2002).

Yan. H.; Park, S. H.; Finklestein, G.; Reif, J. H.; LaBean, T. H., DNA-Templated Assembly of Protein Arrays and Highly Conductive Nanowires, *Science,* 301:1882-1884 (2003)

Yang, X., Wenzler, J. Qi, X. Li and N. C. Seeman, Ligation of DNA Triangles Containing Double Crossover Molecules, *Journal of the American Chemical Society* 120:9779-9786 (1998)

Zanchet, D.; Micheel, C.; Parak, W. and Alivisatos, P. *J. Phys. Chem. B* 106:11758-11763 (2002).

Zanchet, D.; Micheel, C.; Parak, W. and Alivisatos, P. *Nano Lett.* 1:32-35 (2001).

What is claimed is:

1. A two dimensional polynucleic acid array of polygonal units linked together by complementary double cohesive ends, comprising a plurality of polygonal units, wherein:
- each of said polygonal units has, as edges, parallel helices of connected nucleic acid multi-crossover domains along their helix axes;
- each of at least two said edges of each of said polygonal units has ends with two parallel double helices;
- each of said two parallel double helices terminate in a cohesive end to provide a double cohesive end at each end of said at least two edges, whereby said double cohesive end of one edge of a polygonal unit is cohered to a complementary double cohesive end of an adjacent polygonal unit in the array to form an extended edge linking together two adjacent polygonal units; and
- at least one edge, which is different from said at least two edges, of a subset of said polygonal units has at least one end which is attached to a nanoparticle or pendant molecule.

2. The two dimensional polynucleic acid array of claim 1, wherein said nucleic acid multi-crossover domains are double crossover domains.

3. The two dimensional polynucleic acid array of claim 1, wherein said nucleic acid multi-crossover domains are triple crossover domains.

4. The two dimensional polynucleic acid array of claim 1, wherein said polygonal unit is a triangle.

5. The two dimensional polynucleic acid array of claim 1, wherein the cohesive ends on said two parallel helices are different.

6. The two dimensional polynucleic acid array of claim 1, wherein said polygonal units are triangles having as edges connected nucleic acid double crossover domains.

7. The two dimensional polynucleic acid array of claim 1, wherein said polygonal unit is a triangle having as edges connected nucleic acid triple crossover domains.

8. The two dimensional polynucleic acid array of claim 1, wherein said polygonal unit is a six helix bundle.

9. The two dimensional polynucleic acid array of claim 8, wherein two edges of said six helical bundle polygonal unit are cohered to two edges of an adjacent six helix bundle polygonal unit in the array via double cohesive ends to form two extended edges linking together two adjacent six helix bundle polygonal units.

10. The two dimensional polynucleic acid array of claim 1, wherein each polygonal unit of said subset of polygonal units has at least one end which is attached to a nanoparticle.

11. The two dimensional polynucleic acid array of claim 10, wherein said nanoparticle is a gold nanoparticle.

12. The two dimensional polynucleic array of claim 10, wherein said nanoparticle is a CdSe nanoparticle.

13. The two dimensional polynucleic acid array of claim 10, wherein said subset of said polygonal units having at least one end attached to a nanoparticle is periodically arranged in the array.

14. The two dimensional polynucleic acid array of claim 10, wherein said subset of said polygonal units is a mixture of polygonal units having at least one end attached to one of at least two different nanoparticles or one of at least two nanoparticles of different sizes.

15. The two dimensional polynucleic acid array of claim 14, wherein said nanoparticles of different sizes are 5 nm and 10 nm gold nanoparticles.

16. The two dimensional polynucleic acid array of claim 10, wherein at least one nanoparticle attached to at least one end of a polygonal unit in said subset is disposed above the plane of the two dimensional polynucleic acid array and at least one nanoparticle attached to at least one end of a polygonal unit in said subset is disposed below the plane of the two dimensional polynucleic acid array.

17. The two dimensional polynucleic acid array of claim 1, wherein each polygonal unit of said subset of said polygonal units has at least one end which is attached to a pendant molecule.

18. The two dimensional polynucleic acid array of claim 17, wherein said subset of said polygonal units having at least one end attached to a pendant molecule is periodically arranged in the array.

19. The two dimensional polynucleic acid array of claim 17, wherein said subset of said polygonal units is a mixture of polygonal units having at least one end attached to one of at least two different pendant molecules.

20. The two dimensional polynucleic acid array of claim 17, wherein at least one pendant molecule attached to at least one end of a polygonal unit in said subset is disposed above the plane of the two dimensional polynucleic acid array and at least one pendant molecule attached to at least one end of a polygonal unit in said subset is disposed below the plane of the two dimensional polynucleic acid array.

* * * * *